(12) United States Patent
Lindgren

(10) Patent No.: US 6,289,716 B1
(45) Date of Patent: Sep. 18, 2001

(54) METHOD FOR ON-LINE ASSESSMENT AND INDICATION OF TRANSFORMER CONDITIONS

(75) Inventor: Stanley R. Lindgren, Sunnyvale, CA (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 0 days.

(21) Appl. No.: 09/347,183

(22) Filed: Jul. 2, 1999

Related U.S. Application Data

(60) Provisional application No. 60/097,088, filed on Aug. 19, 1998, and provisional application No. 60/097,092, filed on Aug. 19, 1998.

(51) Int. Cl.[7] .................................................. G01N 31/08
(52) U.S. Cl. ................................................................ 73/19.1
(58) Field of Search ................................. 73/19.1, 23.36, 73/863.81, 863.86, 53.05, 23.25, 23.57

(56) References Cited

U.S. PATENT DOCUMENTS

| 3,111,388 | * | 11/1963 | Horelick et al. . |
| 3,680,359 | * | 8/1972 | Lynch . |
| 4,141,237 | * | 2/1979 | DeFord et al. ....................... 73/23.27 |
| 4,512,181 | * | 4/1985 | Ayers et al. ......................... 73/23.27 |
| 4,587,834 | | 5/1986 | Fisher ..................................... 73/23.1 |
| 5,417,821 | | 5/1995 | Pyke ................................... 204/153.1 |
| 5,591,321 | | 1/1997 | Pyke ....................................... 205/787 |
| 5,659,126 | | 8/1997 | Farber .................................. 73/19.02 |

* cited by examiner

Primary Examiner—Robert Raevis
(74) Attorney, Agent, or Firm—Flehr Hohbach Test Albritton & Herbert LLP

(57) ABSTRACT

There is described a method of monitoring the fault gases in the headspace of a transformer and providing an indication of transformer conditions.

1 Claim, 1 Drawing Sheet

METHOD FOR ON-LINE ASSESSMENT AND INDICATION OF TRANSFORMER CONDITIONS

This application claims priority to Provisional Application Nos. 60/097,088 and 60/097,092, both filed on Aug. 19, 1998, and both entitled "Method for On-Line Assessment of Transformers.

BRIEF DESCRIPTION OF THE INVENTION

This invention relates in general to a method of on-line detection of fault gases in a transformer head space to provide an assessment and indication of the transformer operating conditions.

BACKGROUND OF THE INVENTION

Transformers generally consist of copper and/or aluminum conductors, insulated with paper or varnish, wound into a variety of winding configurations, separated by pressboard spacers to allow oil flow for cooling, and a variety of pressboard barriers for insulation between windings and ground. A silicon steel laminated core links the windings. The assembly is contained in a heavy steel tank with porcelain bushings to connect to the windings, external cooling heat exchangers, and various accessories. The transformer is filled with insulating oil to provide insulation and to carry away heat from the windings. Provisions are made for expansion and contraction of the oil with temperature changes due to loading and ambient. In addition, air and moisture are excluded from the system in order to maintain dielectric integrity and avoid excessive aging of the materials.

Starting in the early 1960s, the practice of monitoring selected gases dissolved in the oil to diagnose operating problems inside oil-filled transformers became a normal industry practice. Various types of dielectric or excessive heating problems break down the insulating oil and solid materials into characteristic gases that dissolve in the oil and collect in the head space. It became industry practice for users to take periodic oil samples from transformers for testing in a laboratory to identify developing operating problems. Considerable effort over the years has gone into trying to categorize certain gases and ratios of these gases to interpret the oil samples and diagnose problems. Because of high variability between different samples, different laboratories, different lab tester, it has been generally considered an "art" subject to different diagnoses from different laboratories. An on-line transformer gas monitor has been the "holy grail" for power transformer users.

It is generally known that an arc under insulating oil generates acetylene gas ($C_2H_2$) along with a much larger quantity of hydrogen ($H_2$). It is probable that hydrogen bubbles are produced that rise to the top of the transformer faster than the gas can be absorbed into the oil. It is also probable that acetylene rides up with the hydrogen bubbles and therefore will be present throughout the transformer head space rather quickly. Gases diffuse much faster throughout gas than through oil, and the fault gases are uniformly distributed in the headspace, whereby a sample is representative of the headspace mixture. Also, transformer winding cooling ducts and insulation barriers tend to provide a vertical path for cooling oil flow and for "rising" bubbles in "rising" oil flow to the top of the transformer. This contrasts with a highly restricted and possible totally blocked horizontal oil path in large power transformers with directed oil flow. For fault gases to get from the point of generation deep in the windings to a location on the tank wall where an oil sample is typically taken, or an on-line analyzer may be located, the gases most likely transfer from rising oil to the gas head space first and then back into the oil at the interface. Interfacial transfer takes place in accordance with the relative saturation Ostwald coefficients for the individual gases. Thermosyphon action alone, no pumping, will slowly circulate oil near the head space, it takes quite some time to reach some degree of equilibrium with the head space, throughout the transformer. It may take 24 hours or more for the fault gases caused by an arc deep in the windings to reach the tank wall where an oil sample is taken or an on-line gas analyzer may be located. Pumped oil circulation will reduce this time, however even then significant time will elapse before any of the fault gases generated by the initial arc can be sensed at the tank wall. During this amount of time, a catastrophic failure of the transformer can develop. Close monitoring of the head space gases for rapidly increasing levels of acetylene and hydrogen would provide an indication of arcing and could be used to generate a dangerous condition and/or a trip signal.

Other failure modes in aged transformers that happen due to cumulative effects of aging, shrinkage, loose clamping, and winding deformation are associated with through-faults (short circuits). The tendency is for individual conductors to bend and twist mechanically during through-faults. Failure may occur several days, weeks or months after the "final" through-fault. Failure starts with shorted turn or strands, resulting in very high localized current, not sensed by differential relaying, and there may not be any partial discharge activity involved. There is burning of conductor and strand insulation and generation of CO and ethylene. This may even include acetylene without arcing. Close monitoring of the head space gases after a through-fault could be used to generate an indication of failure and to generate a trip signal. Here again, bubbles and debris may reach some critical stress region and cause a major failure. This can be a high energy arc that causes tank rupture. Through-fault failures are probably the most difficult to detect because deformed winding conductors can be extremely close together and appear normal. Voltage between turns ranges from a few volts to hundreds of volts. The slightest oil space will provide adequate insulation. However, the slightest movement turns the situation into a serious problem. Close monitoring of the head space gases for a sudden spike in CO, ethylene, and possibly acetylene can be sensed as a dangerous and/or trip condition.

Other gases are generated very slowly by low energy partial discharges or pyrolysis of insulating materials that might dissolve into the oil rather than form bubbles. These are typically incipient problems that would be considered cause for caution and merit more frequent and closer monitoring. In general, a "change" in the long-term trend of gassing is cause for alarm. "Unchanging" low levels of gases, other than acetylene, are normally considered as a "normal" operating condition.

Pat. No. 5,659,126 describes a method for monitoring dissolved gases in the electrical insulating oil supply of an electrical transformer in which a blanket of gas containing a fault gas is present in the headspace above the insulating oil supply contained in the transformer. The method includes transferring a sample of the gas from the headspace to a gas chromatograph instrument, and measuring by gas chromatograph techniques the gas concentration level of the fault gases contained in the gas sample. The output from the gas chromatograph is processed by a computing device which calculates the related gas concentration level of the fault gases present in the oil supply. The computing device is informed of a partition function based on Henry's Law and converts the measured fault gas concentration level in the headspace to a measurement of the corresponding concentration level of the same fault gas in the oil supply. The resulting data are used for producing a reading of the fault gas concentration in the transformer oil supply to provide an indication of a specific transformer fault. The problem with measurement of dissolved or headspace gases is that there are many factors, including temperature, pressure, existing degree of saturation, and partitioning coefficients of individual gases that affect the concentration of the dissolved gases present in the oil and the gases in the head space. It is very difficult to sense an unchanging gas condition because of the dynamic changes in gas distribution through out the transformer.

It would be very valuable to have a way to identify normal and cautious operating conditions without having to take into account all of the variables. Certain gases are slowly and consistently generated over the years in all operating transformers. $CO_2$ is an example. The concentration may vary in the head space as temperature and pressure vary even though the total volume of $CO_2$ in the transformer is essentially constant on a weekly/monthly basis. Considerable attention has been given over the years to interpreting transformer faults based upon the ratios of the various fault gases. This relates to the different generation rates of the individual gases at specific local oil temperatures. Generally, more than one gas is produced by any fault condition. However, these efforts were typically based upon oil samples tested in a laboratory, not on-line at the transformer. Also, it is typically assumed that equilibrium conditions exist between the gas producing problem, all of the oil in the transformer and between that oil and the head space gases. In reality, it is very doubtful that equilibrium ever exists in an operating transformer because of variations in load, ambient temperature pumped oil flow and thermosyphon oil flow. It is next to impossible to interpret gases this way reliably on a short time basis. $CO_2$, or an introduced known volume of a tracer gas, can be used as a base reference. By comparing fault and oxygen gases to nitrogen, being essentially 100%, and the varying $CO_2$ concentration related to temperature, pressure, oil circulation and its saturation characteristic, the varying concentrations of other gases can be compared in a way that reveals whether total gas content in the transformer is changing, plus how fast it is changing, as an indicator of a gas generation condition inside the transformer. The significance of such "true" changes, once identified, is well established by experience in the industry. This would provide a means for reliable determination of normal (green), cautious (yellow) or dangerous (red) operating conditions.

OBJECTS AND SUMMARY OF THE INVENTION

It is a general object of the present invention to provide a method for on-line assessment and indication of transformer conditions.

It is another object of the present invention to provide on-line assessment of and indication of transformer conditions which is substantially independent of external factors such as temperature, pressure, saturation and partitioning coefficients of the individual gases in the headspace.

It is another object of the present invention to provide a method of assessing transformer conditions which can adequately remove all variables from an assessment to provide reliable assessment on a real-time basis.

In one aspect, the present invention relates to a method of preventing catastrophic failure of transformers due to arcing which comprises detecting rapidly increasing levels of hydrogen together with traces of acetylene in the headspace of a transformer and providing an alarm and/or trip signal.

In another aspect, the present invention relates to a method of assessing transformer conditions which comprises establishing a known volume of a reference gas or tracer gas in the operating transformer and comparing the fault and oxygen gases to the varying concentration of the reference or tracer gas related to pressure, temperature, etc. to provide an indication of whether the gas composition in the transformer is changing, and the rate of change.

BRIEF DESCRIPTION OF THE DRAWINGS

The invention will be clearly understood from the following description when read in conjunction with the accompanying schematic diagram labeled FIG. 1.

DETAILED DESCRIPTION OF THE INVENTION

Figure 1:
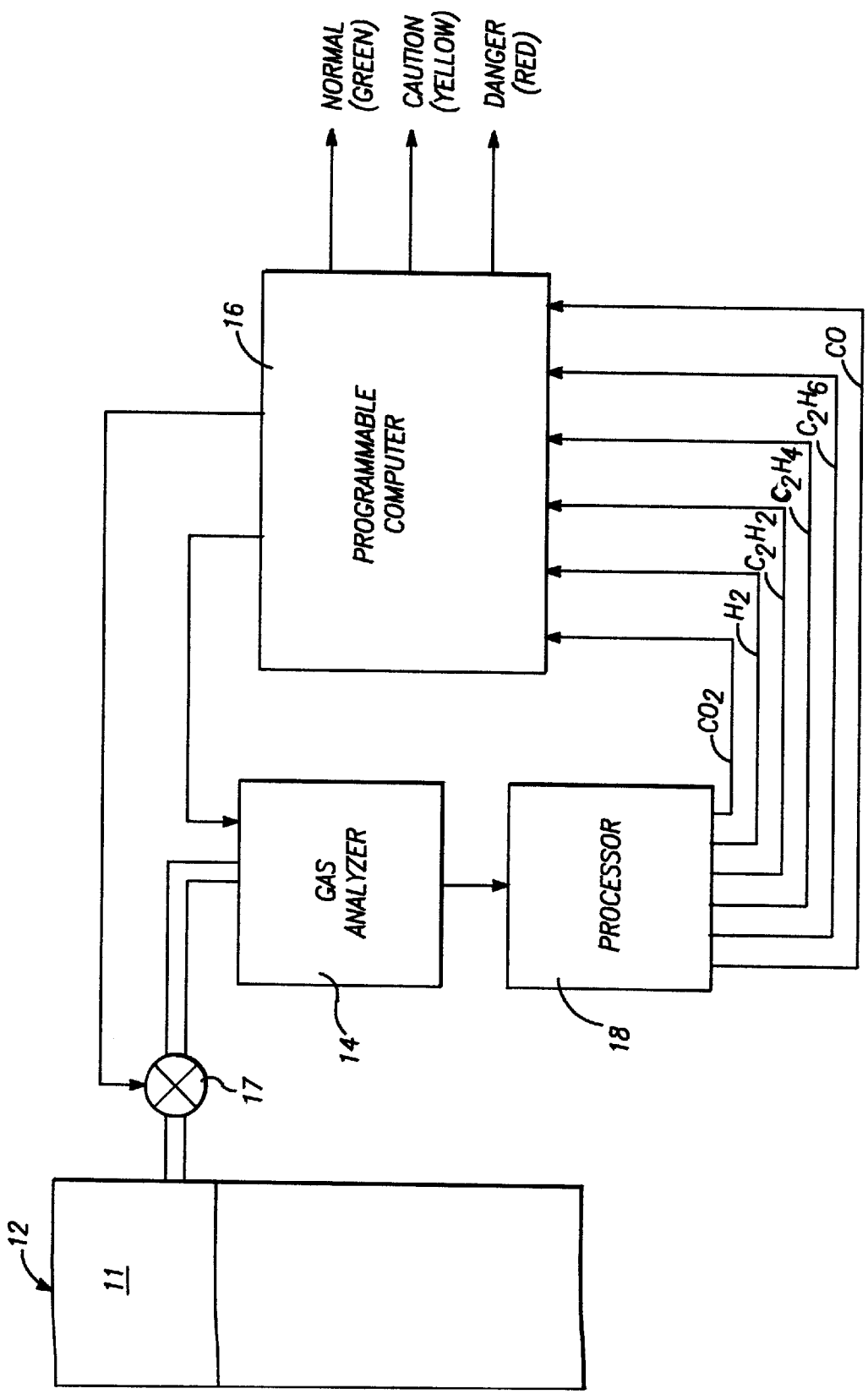

The present invention provides a system and method for on-line assessment of and indication of transformer conditions. Faults in a transformer, such as arcing, corona discharge, insulation failure, etc., result in gases which can be used to identify faults and provide an indication of the transformer condition. Fault gases typically present in gas samples include ethane ($C_2H_6$), ethylene ($C_2H_4$), acetylene ($C_2H_2$), methane ($CH_4$), carbon dioxide ($CO_2$), carbon monoxide (CO) and hydrogen ($H_2$). Dry nitrogen is generally added to the headspace.

Referring to FIG. 1, gases in the headspace 11 of transformer 12 are periodically sampled and applied to a gas analyzer 14. The sampling is controlled by the programmable computer 16 which controls the sample valve 17. The computer also controls operation of the gas analyzer 14. The gas analyzer is preferably a gas chromatograph. The output signal from the gas analyzer is applied to a processor 18 which operates on the signal and provides output signal which are a measurement of the concentration of each fault gas in the gas sample. The measurement is preferably in parts per million (ppm) of the fault gas per volume of the gas in the gas sample. The individual fault gas concentration measurements are applied to the programmable computer.

As described above, an arc in the transformer under the insulating oil generates acetylene gas along with a large quantity of hydrogen. The gas bubbles rise to the top and enter the headspace. By monitoring these gases in the headspace a warning signal can be generated and the transformer taken out of service, thereby avoiding catastrophic damage to the transformer and associated power system. To this end, the programmable computer is programmed to detect sudden increases in the hydrogen and acetylene concentrations and to provide an output danger (red) signal which can be used to automatically disconnect the transformer.

Also as previously described, failures of aged transformers can also be caused by through faults (short circuits). Such faults generate fault gases which rise to the headspace. Generally, a change in the long term trend of gassing is a cause for alarm. However, the concentration of the fault gases can change as a result of changes in temperature, pressure, etc. Any system which is intended to provide warning or caution signals because of changes in long term trends must take this into account. In accordance with one aspect of the present invention, this is achieved by using a reference gas such as the $CO_2$ in the headspace or by introducing a known volume of a tracer gas into the head space. The volume of $CO_2$ in the headspace can be the reference gas since its volume is essentially constant on a weekly/monthly basis. The fault gas concentration is compared by the computer to the changing reference gas concentration due to temperature, pressure, etc., thereby eliminating the effects of temperature, pressure, etc., on the fault gas concentration and give a true indication of any changes. This would then provide a reliable indication of transformer conditions.

To this end, the computer is programmed to receive the measure of gas concentration including reference gas concentration, carbon dioxide in the present example, and perform the comparison. If the fault gases show changes above those due to temperature, pressure, etc., the computer provides an output caution (yellow) signal. If there are no changes, the output will show a normal (green) condition.

The computer 16 may be programmed so as to analyze the gases for hydrogen and acetylene more often than for other gases which change more slowly. Thus, danger or red conditions which occur are monitored so as to detect arcing and provide a timely alert.

Substantial benefits can be obtained by loading power transformers beyond current practices that are based on nameplate ratings and thermal algorithms that are general in nature and usually conservative. Generation of ethylene, ethane and/or CO generally results from excessive heating due to leakage flux, a defective connection or other abnormal condition directly related to transformer loading. Reliable detection of a true increase in any or all of these gases can be related to daily loading events and be used as a precursor of true short-term and continuous loading limits and initiate the cautious condition. Dynamic experience gained from a population of on-line monitors could evolve criteria for loading families of transformers beyond nameplate rating in addition to establishing specific limits for individual units.

Thus, there has been provided a reliable fast-response method for on-line assessment and indication of transformer conditions. The method can generate signals indicating dangerous conditions requiring removal of the transformer from service, or cautious conditions for assessing load conditions and providing criteria for long term operating and loading of the transformer.

What is claimed is:

1. The method of on-line assessment of transformer conditions comprising:

periodically transferring a sample of gas in the transformer headspace to a gas analyzer, operating the gas analyzer to provide signals representing the amount of selected gases in the gas sample including at least hydrogen and acetylene, processing the output signal to provide a measure of the concentration of the selected gases in the gas sample, programming a programmable computer to 1) detect rapid changes in the measured concentration of acetylene and hydrogen and provide a danger output signal, and 2) to compare the varying concentrations of fault gases to the varying concentration of a reference gas as related to temperature, pressure and other variables, and provide output signals indicating normal or cautious transformer conditions, providing the programmable computer with the output signals of the selected gases whereby the computer can process the measured concentration and provide output signals representing the transformer conditions.

* * * * *